United States Patent [19]
Smith

[11] Patent Number: 5,929,318
[45] Date of Patent: Jul. 27, 1999

[54] SYSTEM AND METHOD FOR SENSING LOW LEVELS OF A PARTICULAR GAS IN AN ATMOSPHERE

[75] Inventor: Richard A. Smith, Spring Grove, Ill.

[73] Assignee: Illinois Instruments, Inc., Ingleside, Ill.

[21] Appl. No.: 08/850,640

[22] Filed: May 2, 1997

[51] Int. Cl.⁶ ............................. G01N 7/00; G01N 27/26
[52] U.S. Cl. ............................. 73/23.2; 204/426
[58] Field of Search ................ 73/23.2, 864.81; 205/782; 364/477.01; 204/425, 426

[56] References Cited

U.S. PATENT DOCUMENTS

| | | | |
|---|---|---|---|
| 3,219,046 | 11/1965 | Waugh | 137/8 |
| 3,807,425 | 4/1974 | Boirum et al. | 137/110 |
| 4,562,723 | 1/1986 | Hubner | 73/23.2 |
| 4,569,223 | 2/1986 | Hubner | 73/23.2 |
| 4,642,296 | 2/1987 | Hubner | 73/23.2 |
| 4,720,993 | 1/1988 | Sukhyinder | 73/23 |
| 4,977,916 | 12/1990 | Ohmi et al. | 137/8 |
| 5,101,824 | 4/1992 | Lekholm | 128/419 PG |
| 5,113,892 | 5/1992 | Hull et al. | 137/62 |
| 5,159,951 | 11/1992 | Ono et al. | 137/486 |
| 5,314,007 | 5/1994 | Christenson | 165/43 |
| 5,325,861 | 7/1994 | Goulding | 73/863.83 X |
| 5,336,058 | 8/1994 | Yokoyama | 417/299 |
| 5,345,774 | 9/1994 | Mount | 62/127 |
| 5,419,924 | 5/1995 | Magashima et al. | 427/248.1 |
| 5,421,365 | 6/1995 | Matsuo et al. | 137/599 |
| 5,571,978 | 11/1996 | Gysi et al. | 73/865.8 |

*Primary Examiner*—Hezron Williams
*Assistant Examiner*—Jay L. Politzer
*Attorney, Agent, or Firm*—Jon Carl Gealow

[57] ABSTRACT

A sensor system and method for measuring very low levels of a particular gas in an atmosphere which initially has high level of the gas. A pair of sensors of the particular gas are provided, one of which senses high levels of the particular gas and the other of which senses very low levels. The sensor which senses very low levels of the gas is not exposed to the atmosphere until the gas level has reached a low level, thereby enabling it to more quickly respond to further reduction in the gas.

19 Claims, 3 Drawing Sheets

SYSTEM AND METHOD FOR SENSING LOW LEVELS OF A PARTICULAR GAS IN AN ATMOSPHERE

FIELD OF THE INVENTION

The present invention relates to a system and method for detecting a low level percentage of a particular gas in an atmosphere in a more efficient manner. More particularly it relates to a system and method for more efficiently detecting when the oxygen content in an atmosphere reaches a desired low level from an initial high level.

BACKGROUND OF THE INVENTION

It is well known that numerous manufacturing processes must be conducted to in precisely controlled atmospheres. For instance, a portion of the manufacturing process for electronic semiconductor devices is carried out in ovens in which the atmosphere must contain very low levels of oxygen. Some such processes require oxygen levels in the single digit part per million range. When the oven is first placed in operation, the oxygen level therein is that of the earths atmosphere, i.e. approximately 21%. If current available is oxygen sensors capable of measuring parts per million of oxygen in the single digit range are exposed to the typical 21% oxygen content of air, it takes them an exceeding long time to establish their sensitivity in the single digit parts per million range.

That is, the contamination of the sensor with the high level of oxygen prevents it from accurately reading within a reasonable time period single digit parts per million, even though the atmosphere in which it is located has reached the single digit parts per million level of oxygen. While this delay is well known, it has nevertheless been found unacceptable to ignore the failure of the sensor to indicate the desired very low level of oxygen, and to begin processing in the oven based only on the time period during which the oven has been purged of oxygen.

Numerous factors, such as leaks in the oven, variations in the level of oxygen contamination in the oven, and variations in the purity of the purging gas can all contribute to variations from an expected delay period for the atmosphere in the oven to reach the desired very low levels of oxygen. Thus, the considerable delay in the ability of the very low level sensor to accurately indicate the oxygen content of the atmosphere in single digit parts per million, delays the useful operation of the oven, resulting in an overall loss of production time, and therefore increased expense. Accordingly, it would be of considerable advantage to provide a system and arrangement in which a very low level oxygen sensor would more quickly become sensitive to a very low level of oxygen being reached in an atmosphere originally containing the typical 21% oxygen found in air.

SUMMARY OF THE INVENTION

It is an object of this invention to provide a system and method for more efficiently sensing the presence at very low levels of a particular gas in an atmosphere originally containing the particular gas at high levels. It is a further object of this invention to provide such a system and method which is readily manufactured and adapted for use in a manufacturing system. It is still another object of this invention to provide such a system in which the flow path for the sample of the atmosphere being sensed and the sensors is provided in a compact assembly.

A system and method for detecting when the content of a particular gas in an atmosphere reaches a low level from an initial high level in accordance with this invention includes a pair of sensors of the particular gas, one of which sensors is suitable sensitive to high levels of the particular gas, and the other of which sensors is particularly sensitive to very low levels of the particular gas. A manifold provides a controlled flow path for sampling the atmosphere being measured, and supports the pair of sensors. From an inlet in the manifold, the atmosphere sample flows over the sensor sensitive to high levels of the sensed gas. The atmosphere sample then flows through a volume storage area to the input of a first three port solenoid actuated valve formed in the manifold. From the input port of the first valve, the gas flows to a normally open port or to a normally closed port. A second three port solenoid valve formed in the manifold has an output port and an normally open input port and a normally closed input port. The normally open input port is connected to the normally open output port of the first three port solenoid valve. The sensor which is particularly sensitive to very low levels of the particular gas is exposed to a flow path in the manifold which connects the two normally closed paths of the two solenoid valves.

The system includes an electronic control circuit responsive to the output of the sensor responsive to high levels of the particular gas. When the level of the particular gas reaches a certain lower level, the control circuit energizes or actuates the two solenoid valves, thereby closing the normally open ports and opening the normally closed ports. The sensor which is particularly sensitive to very low levels of the particular gas is then exposed to the sample of the atmosphere after it has reached a sufficiently low level of the particular gas such that it will more quickly respond to lower levels, that is parts per million in the single digit range. Both sensors remain active, such that should the sensed gas level at the input to the high level sensor rise above the level at which the solenoid valves are actuated, the solenoid valves will be de-energized to actuate the valves to their normally closed positions.

DETAILED DESCRIPTION OF THE PREFERRED EMBODIMENT

Figure 1:
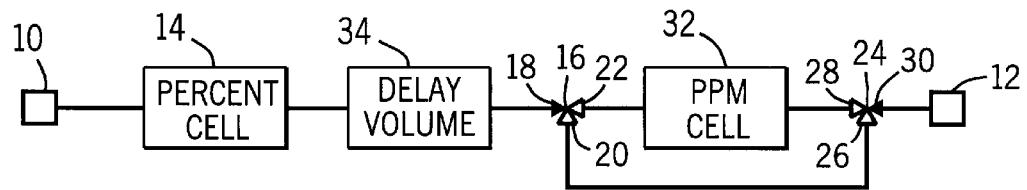
FIG. 1 is a flow diagram of a system for sensing low levels of a particular gas in an atmosphere in accordance with this invention.

Referring to FIG. 1, a sample of an atmosphere in which the presence of a particular gas is to be measured is directed through a flow path from an inlet 10 to an outlet 12. For instance, it is necessary to reduce the level of oxygen in the atmosphere in ovens used to process semiconductors. To determine the level of oxygen in the atmosphere in the oven, a sample stream of the atmosphere is directed through the flow path shown in FIG. 1. The sample stream is first directed from inlet 10 to contact a sensing element of cell of a first sensor 14. The first sensor 14 is selected such that it will readily indicate levels of oxygen from that percentage normally found in air, i.e. 21% down to the range of 1000 parts-per-million (ppm). The flow path continues from the first sensor 14 to one of the ports of a first three way valve 16. The three way valve 16 has three ports 18,20, and 22. The sample stream flowing to port 18 may be directed to flow from either port 20 or 22 depending upon the actuation of the valve 16. A second three way valve 24 also has three ports, 26,28, and 30. Port 30, which is connected to the outlet 12 may receive the sample stream flow from either port 26 or 28 depending upon the actuation of the valve 24.

The three way valves 16 and 24, which are actuated by solenoids as will hereinafter be described, are connected and actuated such that the flow from port 18 may be to port 20 to port 26 to port 30 and then to the outlet 12, or from port 22 to port 28, to port 30 and then to the outlet 12. When the first sensor 14 indicates that the level of oxygen in the sample flow is high, i.e. above 1000 ppm, the three way valves 16 and 24 are in their normal positions such that the flow is through the path between ports 20 and 26. When the first sensor indicates that the level of oxygen in the sample flow has dropped below 1000 ppm, the three way valves 16 and 24 are actuated such that the flow is through the path between ports 22 and 28. Flow in the path between ports 22 and 28 contacts the sensing element of a second sensor 32. The second sensor 32 is selected such that it will readily indicate levels of oxygen in the parts-per-million range, more particularly, as low as 0.1 parts per million. When the second sensor 32 indicates that the oxygen level in the sampled atmosphere has reached the desired low level, an output signal is provided to indicate that the oxygen level has reach the desire low level at which processing in the oven may begin.

Due to the nature of the distribution and flow of the atmosphere in the oven and in the sample flow path, sudden rises in the oxygen content of the atmosphere in the sample flow path may occur. If the flow has been in the path between ports 22 and 28 so as to contact the sensing element of second sensor 32, a sudden rise in the oxygen content contacting the second sensor 32 will cause it to loose its sensitivity to low levels of oxygen in the ppm range until it has been exposed to low levels of oxygen for a considerable period of time so as to be purged of the high level of oxygen which has contaminated its sensor. This undesirable consequence is prevented by providing a storage volume 34 for the sampled atmosphere between the first sensor 14 and port 18 of three way valve 16. Upon detecting a rise in the oxygen level above the actuation level of first sensor 14, the three way valves 16 and 24 will be actuated to their normal condition to divert the flow to the path between ports 20 and 26, thus bypassing the second sensor 32. Due to the volume of the sample atmosphere stored in storage volume 34, the atmosphere with increased oxygen content does not have an opportunity to flow through the path between ports 22 and 28 to contact the sensing element of second sensor 32.

Figure 2:
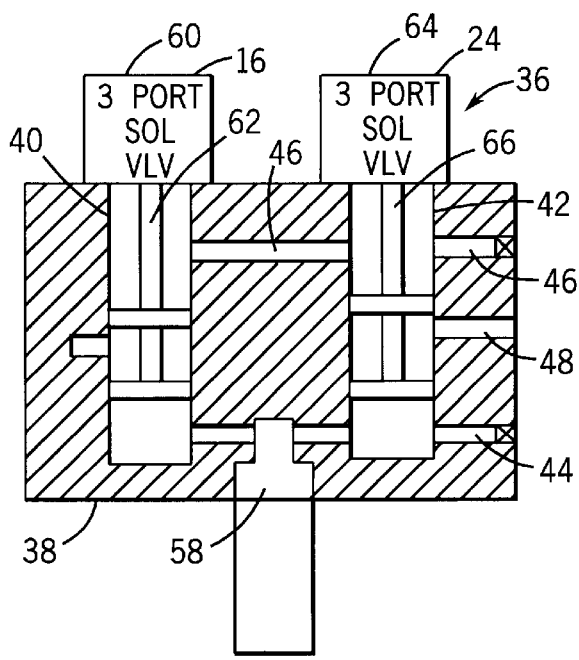
FIG. 2 is a front cross-sectional view of a manifold used in the system of this invention as shown in FIG. 1.
Figure 3:
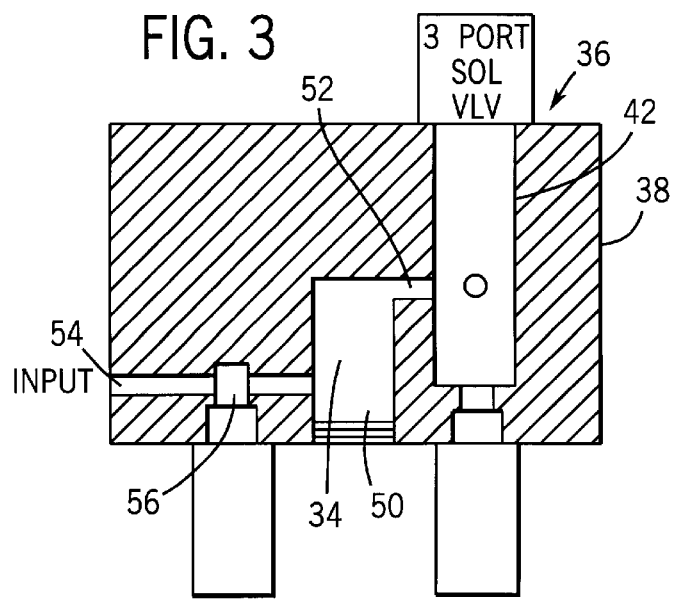
FIG. 3 is a side cross-sectional view of the manifold shown in FIG. 2.
Figure 4:
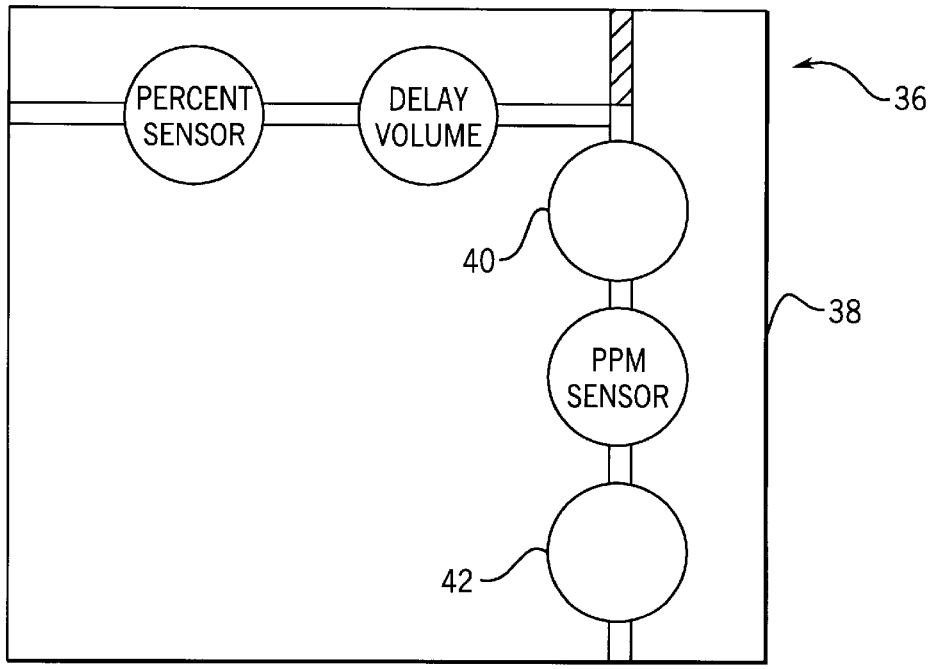
FIG. 4 is a top view of the manifold shown in FIG. 2.

Referring to FIGS. 2, 3 and 4, a manifold assembly 36 which incorporates the major components of the sample flow path of this invention will be described. A solid block 38 of suitable material, such as metal or plastic, is provided with a plurality of bores, some of which intersect with each other. Since the bores are most easily formed by drilling, they are typically cylindrical. Two bores 40 and 42 are formed in the block 38 for receiving the actuatable stems of the three way valves 16 and 24. The axes of bores 40 and 42 parallel and spaced from each other. A pair of smaller diameter bores 44 and 46 parallel to each other extend through the block 38 from one side, through bore 42 and into bore 40. Both of the bores 44 and 46 are plugged at the side of the block, such that they only provide flow paths between the bores 40 and 42. Another bore 48 parallel to bores 46 and 44 enters into bore 42 and forms the outlet 12. Still another larger diameter blind bore 50 is formed in the block 38, with end 50 closed off to form the storage volume 34. A smaller diameter bore 52, the end of which is blocked connects the bore 50, that is the storage volume 34 with the bore 40. Still another smaller diameter bore 54 is provided to enter bore 50, so as to form the inlet 10 and a passageway to the storage volume 34. Finally, bores 56 and 58 intersecting bores 44 and 54, respectively, and are provided for connecting the sensors 14 and 32, and exposing them to the flow of the sample atmosphere.

A solenoid 60 is provided to actuate valve stem 62 of first three way valve 16 between a normal unactuated position shown by dashed lines and an actuated position shown by solid lines. Similarly, a solenoid 64 is provided to actuate valve stem 66 of second three way valve 24 between a normal unactuated position shown by dashed lines and an actuated position shown by solid lines. With both valve stems 62 and 66 in the unactuated positions, flow between the bores 40 and 42 is through bore 46, with flow through bore 44 being blocked, such that the second sensor 32 is not exposed to the flow of the sample of the atmosphere. When both valve stems 62 and 66 are actuated to the positions shown by the solid lines, flow between the bores 40 and 42 is through bore 44, thus exposing the second sensor 32 to the flow of the sample of the atmosphere.

In a preferred embodiment of this invention, the block 38, the attached solenoids 60 and 64, and the attached sensors 14 and 32 are encapsulated, so as to form a unitary structure. Also, in a large measure, the encapsulation prevents the flow of the sample of the atmosphere through unintended paths. With the assembly thus encapsulated, only the inlet and outlet connections for the sample atmosphere flow, and the electrical connections to the two sensors and the two solenoids need be made to connect the system for use in measuring low levels of oxygen in an atmosphere.

Figure 5:
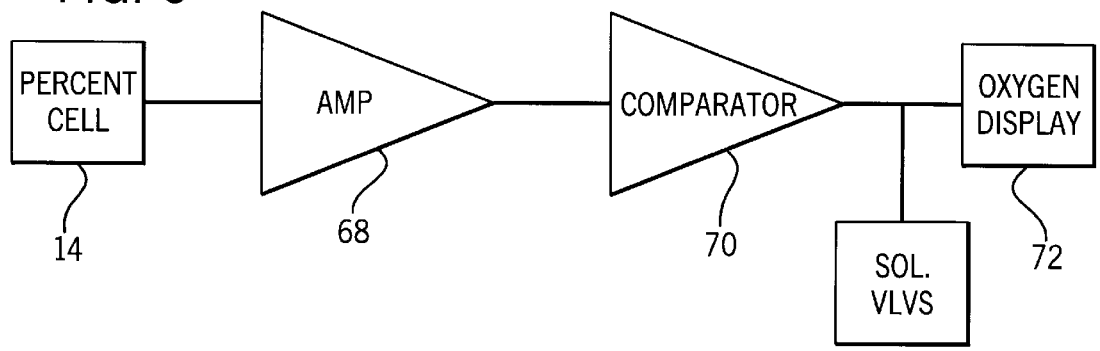
FIG. 5 is a block diagram of the portion of the electronic control circuitry associated with the percentage or higher level sensor in accordance with this invention

Referring to FIG. 5, the output signal of the first oxygen sensor 14 is provided to an operational amplifier 68, the output of which is in turn supplied to a comparator circuit 70. The output of the comparator circuit 70 is supplied to a display device 72 which indicates the oxygen content of the atmosphere when it is greater than 1000 ppm. When the output of the comparator circuit 70 indicates that the oxygen content has dropped below 1000 ppm, the solenoids 60 and 64 are energized to close the flow path through bore 46 and open the flow path through bore 44. Thus, the second oxygen sensor 32 is exposed to the sample atmosphere flow.

Figure 6:
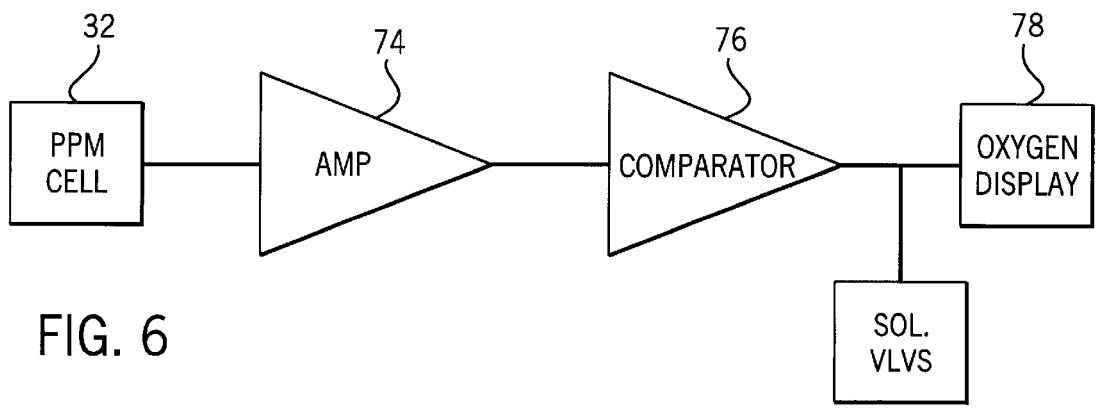
FIG. 6 is a block diagram of the portion of the electronic control circuitry associated with the parts-per-million or lower level sensor in accordance with this invention.

Referring to FIG. 6, the output of the second oxygen sensor 32 is supplied to an operational amplifier 74, the output of which is in turn supplied to a comparator circuit 76. The output of the comparator circuit 76 is supplied to a display device 78 which indicates the oxygen content of the atmosphere when it is less than 1000 ppm. The visual display of the oxygen content can be used to determine when the oxygen content has reached a low enough level to begin processing in the atmosphere being measured. However, in an alternate arrangement the electrical output of the comparator circuit 76 can be used as a signal to start processing in the atmosphere being measured. Further, as an additional control feature, the output of comparator circuit 76 can be used to cause the return of the solenoid valves to their normal positions should the oxygen content raise above 1000 ppm.

Figure 7:
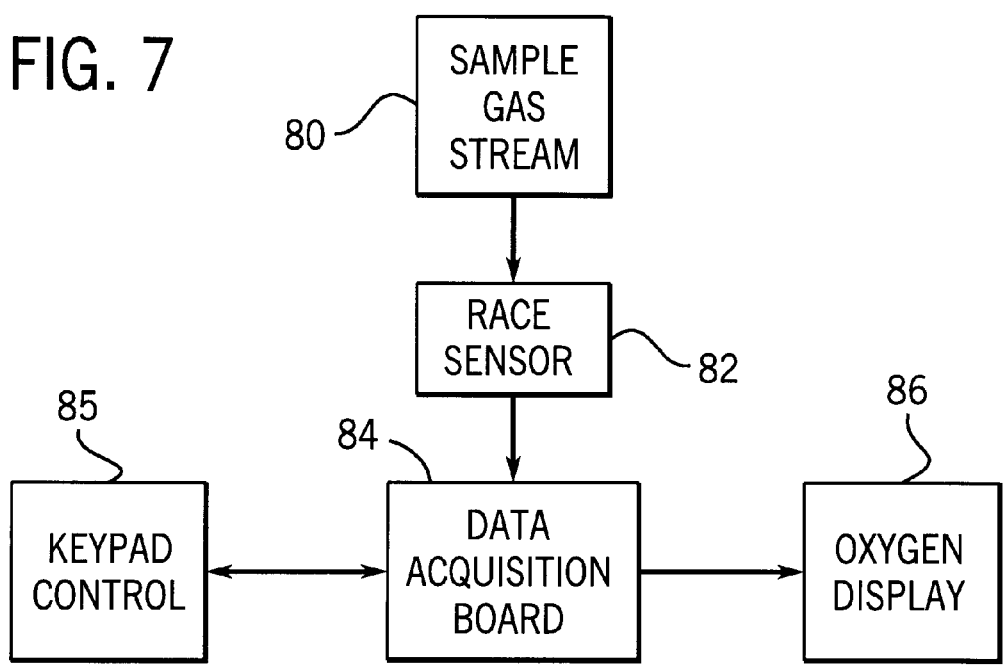
FIG. 7 is a block diagram of an electronic control system for use with an oven which includes the system for sensing the level of a particular gas in an atmosphere in accordance with this invention.

Referring to FIG. 7, an instrumentation system is shown for incorporating the system of this invention in an oven control system. A sample gas stream 80 is provided to the sensor system 82 of this invention. The output of the sensors, is supplied to a data acquisition board 84 which includes the circuit elements shown in FIGS. 5 and 6. A keypad control 85 is provided to input control parameters to the data acquisition board 84. The data acquisition board 84 also provides output signals to the oxygen display 86.

While only one embodiment of the invention has been shown, it should be apparent to those skilled in the art that what has been described is considered at present to be a preferred embodiment of the system and method of this invention for detecting when the content of a particular gas in an atmosphere reaches a low level from an initial high level. In accordance with the Patent Statute, changes may be made in the system and method without actually departing from the true spirit and scope of this invention. For example, the solenoid operated valves could be provided as separate units, with the various flow paths being formed by tubing, rather than as bores in a block as described above. Further, the storage volume could be formed as an elongated piece of tubing. The appended claims are intended to cover all such changes and modification which fall in the true spirit and scope of this invention.

What is claimed is:

1. A system for more rapidly measuring low levels of a particular gas in an atmosphere, which gas is initially at a high level, the system providing a flow path for a representative sample of the atmosphere, said flow path exposing a first sensor of said particular gas to the atmosphere, said first sensor having a sensitivity for measuring high levels of the particular gas, a second sensor of said particular gas, said second sensor having a sensitivity for measuring low levels of the particular gas, a flow path including first and second alternative flow paths, said flow path initially directing the atmosphere flow sample to said first sensor and through said first alternative flow path, said first sensor continuously sensing said atmosphere flow sample and providing an output when the level of the particular gas in the atmosphere reaches a first predetermined low level to direct the atmosphere flow sample to said second alternative flow path which exposes said second sensor to the atmosphere flow sample, said second sensor providing an output when the level of the particular gas in the atmosphere reaches a second predetermined low level, which is lower than said first predetermined low level.

2. The system of claim 1, wherein said flow path includes a storage volume between said first sensor and said alternative flow path.

3. The system of claim 1, including first and second three way valves which are actuated by the output of said first sensor when the level of the particular gas in the atmosphere reaches a first predetermined low level to stop the flow of the sample of the atmosphere through said first alternative flow path and to direct it through said second alternative flow path.

4. The system of claim 3, wherein said first and second three way valves are operable by the energization of solenoids.

5. The system of claim 1, wherein the particular gas is oxygen.

6. The system of claim 1, wherein said first sensor is responsive to level of the particular gas in the percentage range, and said second sensor is responsive to levels of the particular gas in the part per million range.

7. A system for measuring low levels of a particular gas in an atmosphere comprising a flow control arrangement through which a sample flow of the atmosphere is circulated, said control arrangement including an inlet, an outlet, first and second three way valves, said first and second three way valves being operable to form first and second flow paths, first and second sensors responsive to the particular gas, said second sensor being exposed to the circulation of the sample flow through said second flow path, said first sensor being responsive to measure relatively high levels of the particular gas in the atmosphere, and said second sensor being responsive to measure relatively low levels of the particular gas in the atmosphere, said first sensor continuously sensing the sample flow from said inlet to said outlet and providing an output when the level of the particular gas in the sample flow of the atmosphere through said inlet to said outlet reaches a first lower level from a higher level, which output actuates said first and second three way valves to direct the sample flow of the atmosphere from said inlet to said outlet through said second flow path, said second sensor providing an output when the level of the particular gas in the sample flow of the atmosphere through said inlet to said outlet through said second flow path reaches a desired second still lower level.

8. The system of claim 7, wherein said first and second three way valves are operable by the energization of solenoids.

9. The system of claim 7, wherein said flow path includes a storage volume between said first sensor and said second sensor.

10. The system of claim 7, wherein the particular gas is oxygen.

11. The system of claim 7, wherein said first sensor is responsive to level of the particular gas in the percentage range, and said second sensor is responsive to levels of the particular gas in the part per million range.

12. A system for measuring low levels of a particular gas in an atmosphere comprising a flow control arrangement through which a sample flow of the atmosphere is circulated, said control arrangement including an inlet, an outlet, first and second three way valves, and a storage volume, said first and second three way valves being operable to form first and second flow paths, first and second sensors responsive to the particular gas, said second sensor being exposed to the circulation of the sample flow through said second flow path, said first sensor being responsive to measure relatively high levels of the particular gas in the atmosphere, and said second sensor being responsive to measure relatively low levels of the particular gas in the atmosphere, the sample flow being from said inlet to said first sensor and then to said storage volume, said first sensor continuously sensing said sample flow and providing an output when the level of the particular gas in the sample flow of the atmosphere through said inlet to said outlet reaches a first lower level from a higher level, which output actuates said first and second three way valves to direct the sample flow of the atmosphere from said inlet to said outlet through said second flow path, said second sensor providing an output when the level of the particular gas in the sample flow of the atmosphere through said inlet to said outlet through said second flow path reaches a desired second still lower level.

13. The system of claim 12, wherein said first and second three way valves are actuated by solenoids.

14. The system of claim 13, wherein said first and said second three way valves and said storage volume are formed as passageways in a structural member.

15. The system of claim 12, wherein said first sensor is responsive to level of the particular gas in the percentage range, and said second sensor is responsive to levels of the particular gas in the part per million range.

16. The system of claim 1, wherein the particular gas is oxygen.

17. A method for measuring low levels of a particular gas in an atmosphere comprising the steps of providing a sample flow of the atmosphere to a first sensor which is responsive to measure relatively high levels of the particular gas in the atmosphere, said first sensor continuously sensing said sample flow and providing a first output when the level of the particular gas in sample flow of the atmosphere reaches a first lower level from a higher level, directing said sample flow of the atmosphere to a second sensor when said first sensor provides the first output, said second sensor providing a second output when the level of the particular gas in the sample flow reaches a second still lower level.

18. A method for measuring low levels of a particular gas in an atmosphere comprising the steps of providing a sample flow of the atmosphere from an inlet to a first sensor, which is responsive to measure relatively high levels of the particular gas in the atmosphere, to a first alternative path, and to an outlet, said first sensor continuously sensing said sample flow and providing a first output when the level of the particular gas in sample flow of the atmosphere reaches a first lower level from a higher level, directing said sample flow of the atmosphere from the inlet to the first sensor, through a second alternative path to a second sensor, to the outlet when said first sensor provides the first output, said second sensor providing a second output when the level of the particular gas in the sample flow reaches a second still lower level.

19. The method of claim 18, for measuring low levels of a particular gas in an atmosphere comprising the of directing the sample flow of the atmosphere through a storage delay volume located between the first sensor and said first and second alternative flow paths.

\* \* \* \* \*

UNITED STATES PATENT AND TRADEMARK OFFICE
CERTIFICATE OF CORRECTION

PATENT NO.   : 5,929,318  
DATED        : July 27, 1999  
INVENTOR(S)  : Richard A. Smith Page 1 of 1

It is certified that error appears in the above-identified patent and that said Letters Patent is hereby corrected as shown below:

Replace Fig. 2 of the patent by the following Fig. 2.

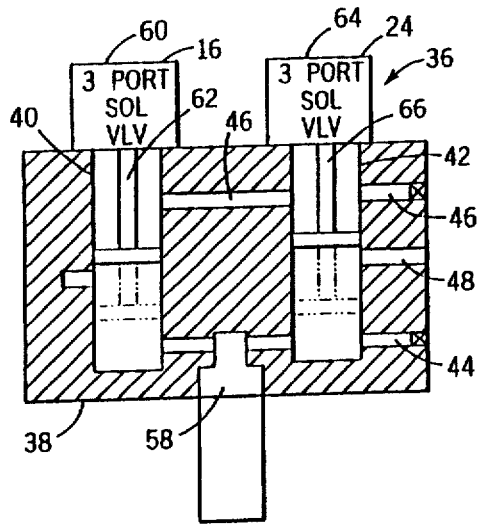

FIG. 2

Signed and Sealed this

Seventh Day of August, 2001

*Attest:*

*Attesting Officer*

NICHOLAS P. GODICI  
*Acting Director of the United States Patent and Trademark Office*